United States Patent
Henseler et al.

(10) Patent No.: US 10,668,194 B2
(45) Date of Patent: Jun. 2, 2020

(54) FLUID PUMP WITH VOLUTE SHAPED HOUSING

(71) Applicant: ReinHeart GmbH, Gütersloh (DE)

(72) Inventors: Andreas Henseler, Simmerath (DE); Roland Graefe, Aachen (DE)

(73) Assignee: REINHEART GmbH (DE)

(*) Notice: Subject to any disclaimer, the term of this patent is extended or adjusted under 35 U.S.C. 154(b) by 145 days.

(21) Appl. No.: 15/771,166

(22) PCT Filed: Oct. 26, 2016

(86) PCT No.: PCT/EP2016/075744
§ 371 (c)(1),
(2) Date: Apr. 27, 2018

(87) PCT Pub. No.: WO2017/076708
PCT Pub. Date: May 11, 2017

(65) Prior Publication Data
US 2018/0328382 A1    Nov. 15, 2018

(30) Foreign Application Priority Data
Nov. 5, 2015 (EP) .................................... 15193212

(51) Int. Cl.
*A61M 1/10* (2006.01)
*F04D 29/44* (2006.01)
*A61M 1/12* (2006.01)

(52) U.S. Cl.
CPC ........ *A61M 1/1012* (2014.02); *A61M 1/1017* (2014.02); *F04D 29/445* (2013.01); *A61M 1/122* (2014.02); *F05D 2250/70* (2013.01)

(58) Field of Classification Search
CPC ... A61M 1/1012; A61M 1/1017; A61M 1/122
(Continued)

(56) References Cited

U.S. PATENT DOCUMENTS

| 4,037,984 A | 7/1977 | Rafferty et al. |
| 5,928,131 A * | 7/1999 | Prem .................... F04D 13/0646 310/90.5 |

(Continued)

FOREIGN PATENT DOCUMENTS

JP    2006167173 A    6/2006

OTHER PUBLICATIONS

International Search Report for corresponding international application No. PCT/EP2016/075744, dated Jan. 20, 2017.
(Continued)

*Primary Examiner* — Amanda K Hulbert
*Assistant Examiner* — Philip C Edwards
(74) *Attorney, Agent, or Firm* — Tarolli, Sundheim, Covell & Tummino LLP (57) ABSTRACT

The present invention relates to a fluid pump that comprises a housing having an inlet opening for receiving the fluid, an outlet opening for discharging the fluid and enclosing an impeller rotating inside the housing to pump the fluid from the inlet opening to the outlet opening and a motor assembly to drive the impeller. The housing is shaped to establish a single turn volute of 360° turn angle providing a first conveying channel located peripherally around the impeller from a fluid entry point at 0° turn angle to a fluid exit point at 360° turn angle of the single turn volute being connected to the outlet opening. The first conveying channel has a first cross section area in radial direction perpendicular to the rotational plane of the impeller, where a size of the first cross section area increases as a monotonic increasing function of the turn angle between entry point and exit point.

13 Claims, 7 Drawing Sheets

(58) Field of Classification Search
USPC .......................................................... 600/16
See application file for complete search history.

(56) References Cited

U.S. PATENT DOCUMENTS

| | | |
|---|---|---|
| 2009/0234447 A1 | 9/2009 | Larose et al. |
| 2014/0171727 A1 | 6/2014 | Nüsser et al. |
| 2014/0205467 A1* | 7/2014 | Yanai ................... F04B 35/04 417/53 |
| 2014/0309481 A1* | 10/2014 | Medvedev .......... A61M 1/1013 600/16 |
| 2015/0005572 A1 | 1/2015 | Reichenbach et al. |

OTHER PUBLICATIONS

International Preliminary Report on Patentability for corresponding international application No. PCT/EP2016/075744, dated Feb. 5, 2018.

* cited by examiner

FLUID PUMP WITH VOLUTE SHAPED HOUSING

RELATED APPLICATIONS

The present invention is a U.S. National Stage under 35 USC 371 patent application, claiming priority to Serial No. PCT/EP2016/075744, filed on 26 Oct. 2016; which claims priority of EP 15193212.6, filed on 5 Nov. 2015, the entirety of both of which are incorporated herein by reference.

FIELD OF THE INVENTION

The present invention relates to a fluid pump with volute shaped housing, a method to manufacture the fluid pump and another method to operate the fluid pump.

BACKGROUND OF THE INVENTION

Fluid pumps are widely used in different technical fields to pump fluids through a conveying system from one point to another point. Fluid pumps might also be used as rotary blood pumps used as ventricular assist devices (VADs) for long-term support comprising an impeller inside the blood pump pumping the blood from an inlet opening to an outlet opening. The main application remains as left ventricular assist device (LVAD) to support the systemic circulation. In the recent years so-called continuous flow devices have completely replaced pulsatile devices for the adult patient population. This is due to a number of reasons including high power density (increased hydraulic output with smaller devices), higher durability, and easier implantation including options for less invasive techniques. Blood pumps cannot be operated at a constant working point (layout point) representing a constant flow of blood over time since the blood flow in human beings strongly varies over time additionally being influenced by further contributing environmental circumstances. A major challenge during the development of a rotary blood pump as a long-term assist device is the bearing design for the impeller inside the blood pump for such operations. One approach is to completely levitate the rotor in the housing in order to avoid a mechanical contact between rotating and stationary parts. An example of a rotary blood pump is given in WO 2014/000753 A1.

During normal operation, the impeller has to be held in a certain position or position range to effectively convey blood. Therefore a bearing has to be applied to compensate forces, e.g. hydrodynamic forces, acting on the impeller during operation. In order to minimize the power consumption for the bearings and/or to simplify the bearing, e.g. requiring less bearing components, the forces acting on the impeller, especially the radially directed forces, during operation should be as small as possible. The principles valid for blood as a pumped fluid can also be applied on other fluids having similar properties.

It would be desirable to obtain a fluid pump, where at least the hydrodynamic radially directed forces acting on the impeller during operation at partial load are smaller compared to fluid pumps according to the state of the art.

SUMMARY OF THE INVENTION

It is the object of the present invention to provide a fluid pump, where at least the hydrodynamic radially directed forces acting on the impeller during operation at partial load are smaller compared to fluid pumps according to the state of the art.

This object is solved by a fluid pump for conveying fluids comprising a housing having an inlet opening for receiving the fluid, an outlet opening for discharging the fluid and enclosing an impeller rotating inside the housing to pump the fluid from the inlet opening to the outlet opening and a motor assembly to drive the impeller, wherein the housing is shaped to establish a single turn volute of 360° turn angle providing a first conveying channel located peripherally around the impeller from a fluid entry point at 0° turn angle to a fluid exit point at 360° turn angle of the single turn volute being connected to the outlet opening, where the first conveying channel has a first cross section area in radial direction perpendicular to the rotational plane of the impeller, where a size of the first cross section area increases as a monotonic increasing function of the turn angle between entry point and exit point, where the monotonic increasing function has an average slope in a first turn angle interval from a first turn angle to the 360° turn angle at the exit point being smaller than the average slope in a second turn angel interval between 0° turn angle and the first turn angle to increase a velocity of the conveyed fluid at least in an area of the first conveying channel assigned to the first turn angle interval.

Here the term "fluid" denotes any fluids suitable to be pumped with the fluid pump according to the present invention, especially viscose fluids with a viscosity of more than 2 mPa*s. In another embodiment, the viscosity is additionally smaller than 5 mPa*s. In a further embodiment the fluid is blood. Blood typically has a viscosity of 3.6 mPa*s.

The term "single turn volute" denotes the inner shape of the housing facing towards the conveyed fluid, where the first conveying channel is arranged in one single turn around the impeller extending from a volute tongue as the start point of single turn also denotes as 0° turn angle of one full (single) turn to the end point also denotes as 360° turn angle of one full (single) turn, where the first conveying channel enters into the outlet opening or into a further channel connected with the outlet opening. The start point of the first conveying channel or volute tongue is also denoted as fluid entry point. Exactly at the 0° turn angle, which is the location of the edge of the volute tongue facing towards the conveyed fluid, the size of the cross section area is nearly zero. Here, the term "size of nearly zero" denotes a size, which is either not present or which is too small to be passed by the fluid or represents a negligible pass rate for the fluid not influencing the flow conditions within the housing. To avoid any misunderstanding, the fluid may exit the impeller comprising blades to convey the fluid at any position between 0° turn angle and 360° turn angle, where the fluid entry point at 0° turn angle denotes the first point, where fluid may enter the conveying channel for flowing around the impeller and leaving the conveying channel within one single turn at the fluid exit point. In an embodiment the blades might be arranged on top of an impeller body carrying permanent magnets in order to be driven by the motor assembly comprising electromagnets in order to apply a drive force to the impeller. The rotational axis denotes the axis of rotation of the impeller, where the rotational plane of the impeller is perpendicular to the rotational axis. In an embodiment the inlet opening is arranged centrally to the impeller. In another embodiment the impeller is arranged to convey the fluid towards the conveying channel through the impeller comprising a top and a bottom plate with blades conveying the fluid arranged between the top and bottom plates. Here either the top or the bottom plate may comprise permanent magnets in order to be driven by the motor assembly comprising electromagnets in order to apply a drive force to the impeller.

The first cross section area of the first conveying channel denotes the area of the first conveying channel seen in radial direction of the impeller further arranged perpendicular to the rotational plane of the impeller. The cross section area may have any suitable shape providing a conveying channel with similar dimensions parallel and perpendicular to the rotational axis of the impeller. The cross section area may be a rectangular, oval or circular area depending on the particular application and fluid. The size of the first cross section area continuously (monotonically) increases from 0° turn angle to 360° turn angle. The increase of the size of the cross section area is described as a function of size depending on the turn angle ranging from 0° turn angle to 360° turn angle. This function of size is denoted as monotonic increasing function. The term "monotonic" denotes the fact that the size as a function of the turn angle will be constant or increases with the turn angle. A monotonic increasing function of the size over the turn angle does not comprise any intervals, where the size decreases when following the conveying channel from the fluid entry point to the fluid exit point.

The monotonic increasing function ranging from 0° turn angle to 360° turn angle is divided into two parts, the second turn angel interval between 0° turn angle and the first turn angle and followed by the first turn angle interval ranging from the first turn angle to the 360° turn angle corresponding with the exit point for the conveyed fluid out of the single turn volute. The monotonic increasing function may have any shape, where the average slope within the first turn angle interval from a first turn angle to the 360° turn angle at the exit point being smaller than the average slope in the second turn angel interval between 0° turn angle and the first turn angle. The monotonic increasing function may consist of two straight lines, where the slope of the first line connecting the first turn angle and the 360° turn angle is smaller than the slope of the second line connecting 0° turn angle and the first turn angle, where the average slope within the first turn angle interval is equal to the slope of the first line, the same also for the second line. In an embodiment, the monotonic increasing function may have a convex shape within the second turn angle interval and another shape in the first turn angle interval, e.g. a straight line with a constant slope smaller than the average slope of the convex line of the second turn angle interval. The term convex shape denotes a function, which second derivate is positive. In other embodiments, the monotonic increasing function may have other shapes than straight lines fulfilling the slope condition as specified above. In another embodiment the monotonic increasing function has a concave shape in the first turn angle interval between the first turn angle and 360° turn angle regardless of the shape of the monotonic increasing function within the second turn angle interval. The term concave shape denotes a function, which second derivate is negative. A concave shape is the opposite shape to a convex shape. In any cases, the first turn angle denotes any suitable turn angle less than 360° to be able to define an interval between the first turn angle and the 360° turn angle of a length>0.

Since the impeller comprises a symmetric arrangement of the blades conveying the fluid from the inlet opening to the outlet opening, the fluid volume leaving the impeller per turn angle interval is approximately equal, the cross section area of the first conveying channel has to increase at least linearly as a function of the turn angle to provide a fluid flowing with a constant velocity, where the slope of the linear increase depends on the design flow rate. By an increase of the cross section area of less than a linear increase per turn angle, the pressure of the fluid will fall resulting in an increase of velocity of the conveyed fluid at least in an area of the first conveying channel, where the increase of the size of the cross section area is below a linear increase, where the slope of the linear increase depends on the design flow rate. This section is denoted as the first turn angle interval. As a result of the increase of velocity of the fluid within the first turn angle interval ending with the 360° turn angle, the resulting fluid caused force acting on the impeller in a radial direction from the area assigned to the first turn angle interval towards the impeller will decrease resulting in a lower overall radial force acting on the impeller in partial load operation. The term "assigned to" denotes the correspondence between a certain position in the first conveying channels and a certain turn angle of the single turn volute at this certain position. The shape of the monotonic increasing function is adapted to obtain resulting radial forces acting on the impeller being below a predetermined first threshold under nominal operation conditions. The first threshold might be set by the acceptable power consumption of the fluid pump or on the properties of the bearing layout providing a sufficient bearing behavior within a certain range of forces acting on the impeller. Therefore in another embodiment the ratio between the sizes of the first cross section areas at the turn angles of 360° and 180° of the single turn volute is less than 1.33.

In addition to the magnitude of the radially directed hydrodynamic forces acting on the impeller, which are reduced by the present invention, also the direction of the forces has an influence on the required layout of the bearings and the performance of the fluid pump. In a preferred situation, the radially directed force should have a direction, which is stable at least within a large range of flow rates provided by the fluid pump. Each pump has a certain layout point (or working point) at a certain flow rate, where the radially directed forces have its minimum. The fluid pump of the present invention provides a radially directed force, which additionally to its reduced magnitude has a stable direction at least for flow rates up to the layout point.

Therefore the fluid pump according to the present invention provides a fluid pump with an impeller, where at least the hydrodynamic radially directed forces acting on the impeller during partial load are smaller compared to fluid pumps according to the state of the art enabling to operate the fluid pump with lower power consumption required for the bearings and/or enabling to simplify the bearing assembly of the fluid pump, e.g. requiring less bearing components.

In an embodiment the first turn angle is located at a 270° turn angle of the single turn volute to provide a first turn angle interval having an extension large enough to significantly accelerate the fluid within the area of the first conveying channel assigned to the first turn angle interval to further reduce the resulting fluid caused force acting on the impeller in a radial direction from the area assigned to the first turn angle interval towards the impeller. In a preferred embodiment the first turn angle is located at a 180° turn angle of the single turn volute. An enlarged first turn angle interval will further reduce the resulting fluid caused force acting on the impeller in a radial direction from the area assigned to the first turn angle interval towards the impeller. In another embodiment the first turn angle might be located at a 90° turn angle of the single turn volute or even less.

In an embodiment the first derivation of the monotonic increasing function has a discontinuity at the first turn angle. In another embodiment the first turn angle of the monotonic increasing function represents an inflection point of the monotonic increasing function. The inflection point represents a change from a linear or convex shape of the monotonic increasing function for turn angles below the first turn angle to a concave shape for turn angles larger than the first turn angle. In case of an inflection point as transition between a convex and concave shape, the second derivation of the monotonic increasing function is zero at the inflection point. The shape of the monotonic increasing function below the first turn angle being a non-concave shape reduces the flow resistance in this other turn angle interval.

In another embodiment the monotonic increasing function increases at least linearly between the 0° turn angle (entry point) and the first turn angle. The linear increase provides a reasonable increase of the size of the first conveying channel within the first few degrees of the turn angle following after the fluid entry point at 0° turn angle further reducing the flow resistance induced by the volute tongue.

In another embodiment the monotonic increasing function has a convex shape between the 0° turn angle and the first turn angle. This shape provides a fluid flow with a constant angular momentum within the in the interval between 0° turn angle and the first turn angle.

In another embodiment the housing is further shaped to provide a second conveying channel around the impeller being arranged between the first conveying channel and the impeller, where the second conveying channel has a second cross section area in radial direction perpendicular to the rotation plane of the impeller, where a size of the second cross section area at the fluid entry point of the single turn volute is larger than a predetermined minimum size. With the presence of the second conveying channel at the fluid entry point at 0° turn angle, the disturbing effect of the volute tongue on the fluid flow is reduced. The cross section of the second conveying channel together with the first cross section of the first conveying channel in the neighborhood of the volute tongue at 0° turn angle enlarges the effective cross section of the combined first and second conveying channels, which reduces the friction forces caused by the viscosity of the conveyed fluid in the neighborhood of the volute tongue at 0° turn angle. As a result of the second conveying channel the overall cross section area (sum of the cross section areas of first and second conveying channel) at 0° turn angle is established by the size of the second cross section area having a certain size. As an additional effect of the presence of the second conveying channel the size of the overall cross section area at 0° turn angle is significantly larger than zero and the radial acting force at a volume flow in a part-load operational range (partial load) of the fluid pump is further reduced.

In another embodiment the second conveying channel has a width in radial direction of the impeller of at least 5%, preferably at least 7%, more preferably at least 10%, of the radius of the impeller. A larger radial distance between volute tongue and impeller reduces the disturbance of the circulation of fluid at 0° turn angle caused by the volute tongue.

The presence of the second conveying channel, especially when having a second cross section area as specified above, also enables to reduce the negative static pressure within the fluid pump. This is in particular advantageous for minimizing the magnitude of the radially directed forces when operating the fluid pump at partial load.

In another embodiment the size of the second cross section area is constant from the fluid entry point at 0° turn angle to the fluid exit point at 360° turn angle of the single turn volute. With this layout of first and second conveying channels, the radial forces acting on the impeller during operation of the fluid pump are overall lowered and the variation of the magnitude of the radial forces as a function of different volume flows (flow rates) during operation of the pumped fluid is decreased.

In another embodiment the fluid is blood and the fluid pump is applied as a blood pump. Blood is a viscose fluid having an average viscosity of 3.6 mPa*s. In case of a blood pump the reduction of the hydrodynamic forces including the radially directed forces acting of the impeller are more important compared to other fluid pumps, because blood pumps are used for human beings and therefore are not easily accessible and have to be operated with minimum power consumption in order to guarantee a long lifetime and reliable operation of the blood pump and with minimized pump size enabled by simplifying the bearing assembly in order to improve the wearing comfort for the patient. In an embodiment of the blood pump having a second conveying channel the size of the second cross section area at the entry point is at least 10 mm$^2$. In a preferred embodiment the size of the second cross section area at the entry point is additionally below 20 mm$^2$. With these sizes of the second cross section areas at 0° turn angle the friction forces between housing and blood is significantly reduced while the ratio between the part of the blood leaving the blood pump after one single turn and the part of the blood circulating through the second conveying channel at least a second time is large enough to provide a sufficient pump efficiency.

In an embodiment of the fluid pump as a blood pump, the blood pump has a layout point being adjusted at flow rates above the average volume flow of blood for human beings, where the layout point denotes the flow rate where a function of radially directed hydrodynamic forces acting on the impeller over a flow rate of pumped blood has its minimum. For flowrates higher than the layout point and for flow rates lower then the layout point, the radially directed hydrodynamic forces acting on the impeller increase. An operation below the layout point is denoted as an operation at partial load. Such blood pumps being mainly operated at partial load are also denoted as oversized blood pumps. Average volume flow rates of blood for human beings are approximately at 5 l/min, where the value may be slightly different for males and females. The layout point can be shifted to higher flow rates by enlarging the inner dimensions of the housing, where the blood is conveyed through. A layout point larger than 5 l/min, for example at 7 l/min, will provide a blood pump with an improved efficiency due to the reduction of the flow resistance caused by the viscosity of blood due to the increased inner dimensions of the conveying housing. Blood pumps with a layout point of 5 l/min may have a cross section area at the exit point of approximately 30 mm$^2$, where such oversized blood pumps may have a cross section area at the exit point of approximately 60 mm$^2$. As a result of the oversizing, such oversized blood pumps are mainly operated at flow rates below the layout point (at least more than 50% of the operational time), since the average volume flow rates of blood for human beings of 5 l/min is below the layout point. Especially when adapting the housing to provide a layout point of 7 l/min, the blood pump is operated nearly all the time (at least more than 90% of the operational time) at or below the layout point. Using a housing according to the state of the art, the radially directed forces will steeply increase for decreasing flow rates within the operational range of partial load, which would be disadvantageous for the bearing layout to bear the impeller, for the required bearing control and for non-disturbed long-time use. The increasing slope of the radially directed forces acting on the impeller depends on the shape of the housing of the blood pump. Applying the design rules as specified for fluid pumps according to the present invention, the forces on the impeller can be reduced significantly to a layout according to the state of the art by simultaneously providing an improved efficient pumping behavior with low friction losses especially for oversized blood pumps. Therefore an oversized blood pump according to the present invention provides an efficient fluid pump, where at least the hydrodynamic radially directed forces acting of the impeller during operation at partial load are smaller compared to fluid pumps according to the state of the art.

The invention further relates to a method for manufacturing a fluid pump for conveying fluids according to the present invention comprising a housing having an inlet opening for receiving the fluid, an outlet opening for discharging the fluid and enclosing an impeller rotating inside the housing to pump the fluid from the inlet opening to the outlet opening and a motor assembly to drive the impeller, comprising the step of establish a single turn volute of 360° turn angle with the housing;

providing a first conveying channel located peripherally around the impeller from a fluid entry point at 0° turn angle to a fluid exit point at 360° turn angle of the single turn volute being connected to the outlet opening, where the first conveying channel has a first cross section area in radial direction perpendicular to the rotational plane of the impeller; and adapting the first cross section area to have a size increasing as a monotonic increasing function of the turn angle between entry point and exit point, where the monotonic increasing function has a concave shape in a first turn angle interval from a first turn angle to the 360° turn angle at the exit point to increase a velocity of the conveyed fluid at least in an area assigned to the first turn angle interval.

The method enables to manufacture a fluid pump with an impeller, where at least the hydrodynamic forces acting of the impeller are smaller compared to fluid pumps according to the state of the art enabling to operate the fluid pump with lower power consumption required for the bearings and/or enabling to simplify the bearing assembly of the fluid pump, e.g. requiring less bearing components.

In an embodiment the method comprises the further step of providing a second conveying channel in the single turn volute arranged around the impeller and arranged between the first conveying channel and the impeller, where the second conveying channel has a second cross section area in radial direction perpendicular to the rotation plane of the impeller, where a size of the second cross section area at the fluid entry point of the single turn volute is larger than a predetermined minimum size. Here the friction forces caused by the viscosity of the conveyed fluid are decreased in order to improve the pumping efficiency. Preferably the cross section area of the second conveying channel is adapted to reduce the friction forces below a second threshold.

The invention further relates to a method for operating a fluid pump for conveying fluids according to the present invention comprising a housing having an inlet opening for receiving the fluid, an outlet opening for discharging the fluid and enclosing an impeller rotating inside the housing to pump the fluid from the inlet opening to the outlet opening and a motor assembly to drive the impeller with at least reduced radial force on the impeller at nominal conditions, wherein the housing is shaped to establish a single turn volute of 360° turn angle providing a first conveying channel located peripherally around the impeller from a fluid entry point at 0° turn angle to a fluid exit point at 360° turn angle of the single turn volute being connected to the outlet opening, where the first conveying channel has a first cross section area in radial direction perpendicular to the rotational plane of the impeller, where a size of the first cross section area increases as a monotonic function of the turn angle between entry point and exit point, comprising the step of increasing a velocity of the conveyed fluid at least in an area assigned to a first turn angle interval from a first turn angle to the 360° turn angle at the exit point by a concave shape of the monotonic increasing function within the first turn angle interval.

The method enables to operate the fluid pump with an impeller, where at least the hydrodynamic forces acting of the impeller are smaller compared to fluid pumps according to the state of the art enabling to operate the fluid pump with lower the power consumption required for the bearings and/or enabling to simplify the bearing assembly of the fluid pump, e.g. requiring less bearing components.

In an embodiment the method further comprises the steps of applying the fluid pump as a blood pump with blood as the fluid, where the blood pump has a layout point, at which a function of radially directed hydrodynamic forces acting on the impeller over a flow rate of pumped blood has a minimum and where the layout point is suitably adjusted to flow rates above the average volume flow of blood for human beings to be able to operate the blood pump mainly at partial load; and mainly operating the blood pump at partial load.

It shall be understood that a preferred embodiment of the invention can also be any combination of the dependent claims with the respective independent claim. Further advantageous embodiments are defined below.

BRIEF DESCRIPTION OF THE DRAWINGS

The aforementioned and other aspects of the invention will also be apparent from and elucidated with reference to the embodiments of the invention described herein after making reference to the drawings.

DETAILED DESCRIPTION OF EMBODIMENTS

Various embodiments of the invention will now be described by means of the Figures.

Figure 1:
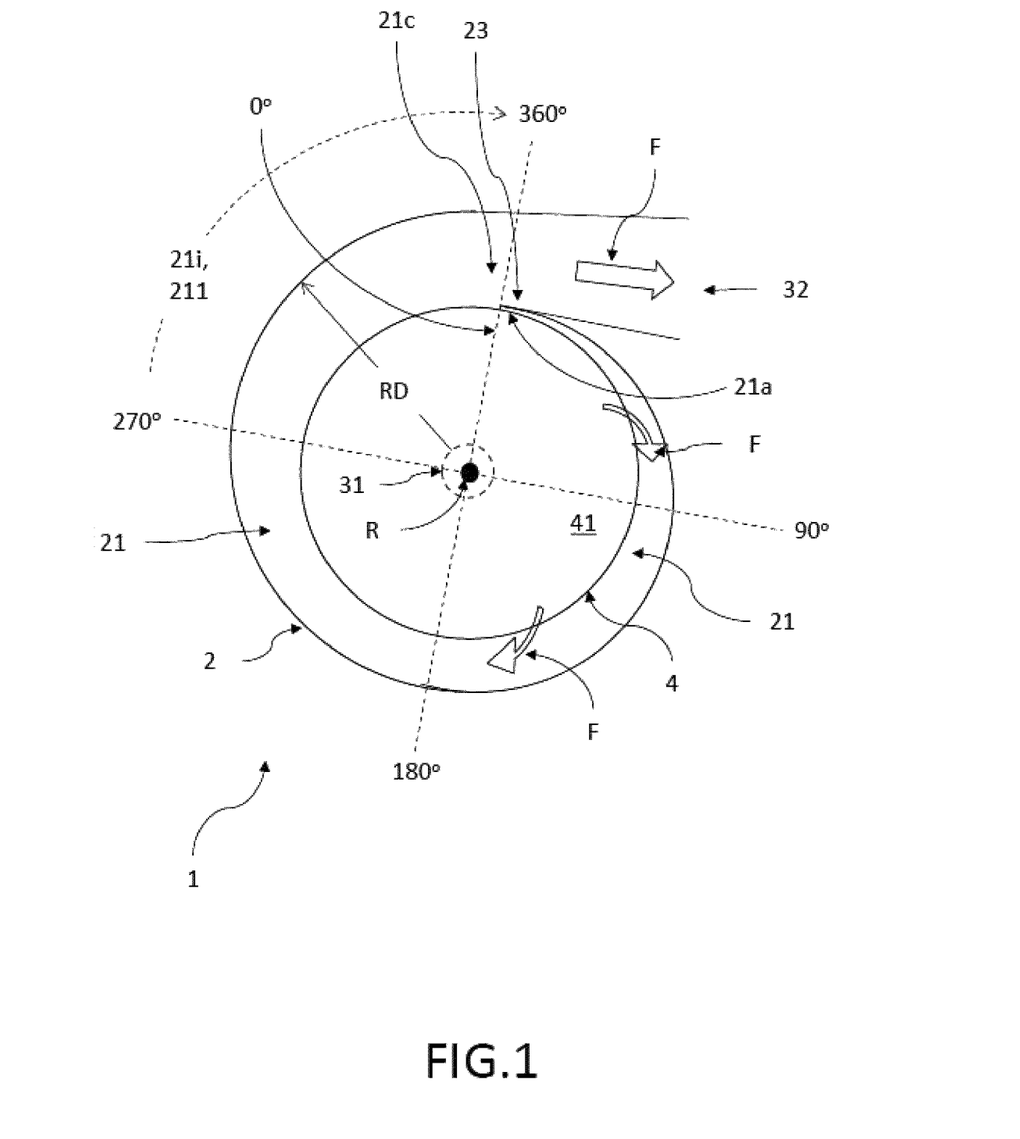
FIG. 1: an embodiment of a fluid pump according to the present invention in a top view onto the rotation plane of the impeller.

FIG. 1 shows an embodiment of a fluid pump 1 for conveying fluids F according to the present invention in a top view onto the rotation plane 41 of the impeller 4. The rotational axis R of the impeller 4 is aligned perpendicular to the rotational plane 41 of the impeller 4. The fluid pump 1 comprises a housing 2 shaped to establish a single turn volute of 360° turn angle with a tongue 23 arranged at 0° turn angle (=fluid entry point) to separate the fluid entry point 21a from the fluid exit point 21c connected to the outlet opening 32. The housing 2 further has a central inlet opening 31 (indicated by dashed circle in the middle of the impeller 4) for receiving the fluid F from the outside and an outlet opening 32 for discharging the fluid F. The housing 2 encloses an impeller 4, which rotates inside the housing 2 to pump the fluid F from the inlet opening 31 to the outlet opening 32. Here the fluid might be conveyed by blades (not shown here) arranged on top of the impeller 4 or might be conveyed through the impeller 4. The impeller 4 is driven by a motor assembly not shown here. The housing 2 provides a first conveying channel 21 located peripherally around the impeller 4 from a fluid entry point 21a at 0° turn angle to a fluid exit point 21c at 360° turn angle of the single turn volute being connected to the outlet opening 32, whereby the first conveying channel 21 has a first cross section area 21F in radial direction RD perpendicular to the rotational plane 41 of the impeller 4. The edge of the tongue 23 facing towards the conveyed fluid F is located at the 0° turn angle. The fluid may exit the impeller 4 at any position between 0° turn angle and 360° turn angle, as indicated by the two bend arrows F extending from the inlet opening 31 towards the housing 2. In order to achieve the advantages according to the present invention, a size of the first cross section area 21F increases as a monotonic function of the turn angle between entry point 21a and exit point 21b, where the monotonic increasing function MIF (see FIG. 5) has an average slope in a first turn angle interval 21i from a first turn angle 21b to the 360° turn angle at the exit point 21b being smaller than the average slope in a second turn angel interval 21s between 0° turn angle and the first turn angle 21b to increase a velocity of the conveyed fluid F at least in an area 211 of the first conveying channel 21 assigned to the first turn angle interval 21i. In an embodiment the monotonic increasing function MIF may have a concave shape in a first turn angle interval 21i. However at the fluid entry point 21a the size of the cross section area might be zero or might be too small to be passed by the fluid or might provide a negligible pass rate for the fluid F not influencing the flow conditions within the housing 2. In an embodiment the fluid pump 1 shown in FIG. 1 is a blood pump with blood as the pumped fluid F.

Figure 2:
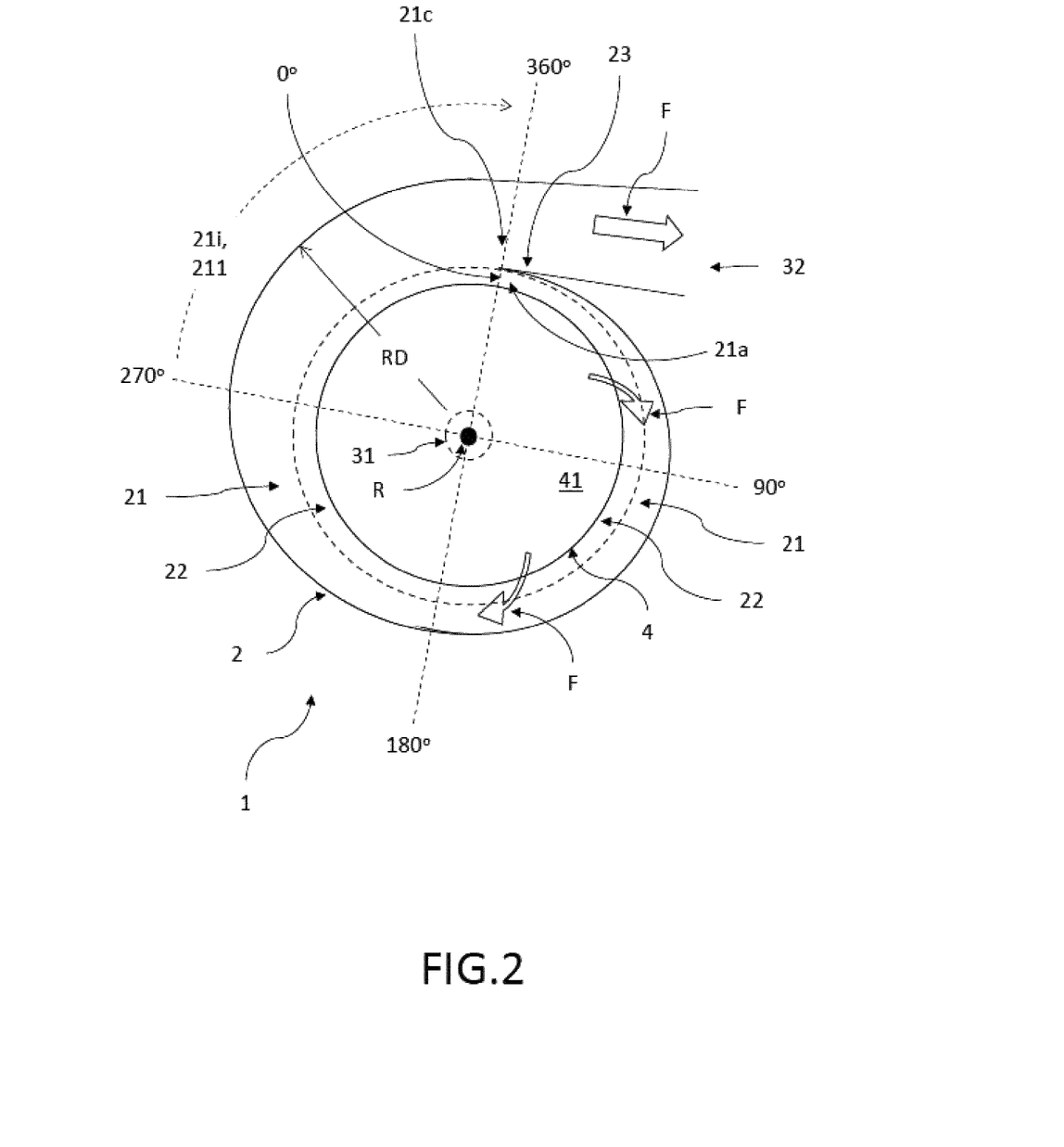
FIG. 2: an embodiment of a fluid pump according to the present invention in a top view onto the rotation plane of the impeller with first and second conveying channels.

FIG. 2 shows an embodiment of a fluid pump 1 according to the present invention in a top view onto the rotation plane 41 of the impeller 4 with first and second conveying channels 21, 22. The rotational axis R of the impeller 4 is aligned perpendicular to the rotational plane 41 of the impeller 4. The fluid pump 1 shown here comprises the same components and areas as shown in FIG. 1, where the housing 2 is furthermore shaped to additionally provide a second conveying channel 22 around the impeller 4 (indicated as dashed circle around the impeller 4) being arranged between the first conveying channel 21 and the impeller 4. Here the second conveying channel 22 has a second cross section area 22F in radial direction perpendicular to the rotation plane 41 of the impeller 4 with a size at the fluid entry point 21a of the single turn volute being large enough to significantly decrease friction forces between fluid F and housing 2 (wall of the first conveying channel 21). Therefore the size of the second cross section area 22F is larger than a predetermined minimum size required to achieve a significant decrease of the friction forces. Especially at the fluid entry point 21a, where the volute tongue 23 is arranged, the size of the cross section area 21F of the first conveying channel 21 is very small or zero causing the friction forces being larger than at other turn angles, where the first conveying channel 21 has larger cross section areas 21F. At the fluid entry point 21a the main contribution to the overall reduction of the friction force could be achieved by introducing the second conveying channel 22 with the second cross section area 22F. In this embodiment the size of the second cross section area 22F is constant from the fluid entry point 21a at 0° turn angle to the fluid exit point 21c at 360° turn angle of the single turn volute. In an embodiment the fluid pump 1 shown in FIG. 2 is a blood pump with blood as the pumped fluid F.

Figure 3:
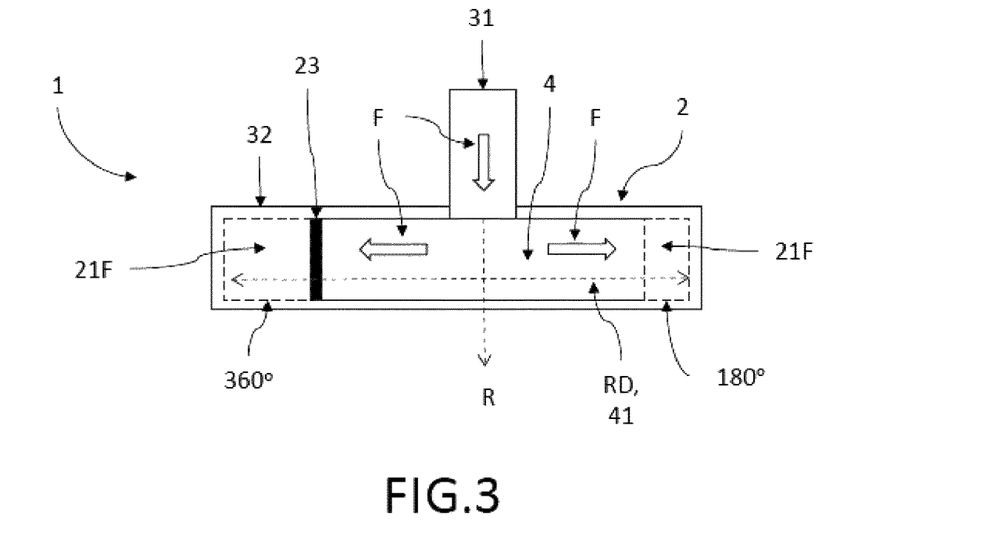
FIG. 3: a schematic view of the first cross section areas of the first conveying channel at 180° turn angle and 360° turn angle in a side view of the fluid pump of FIG. 1.

FIG. 3 shows a schematic view of the first cross section areas 21F of the first conveying channel 21 at 180° turn angle and 360° turn angle in a side view of the fluid pump 1 of FIG. 1. The inlet opening 31 is arranged at a central position with respect to the impeller 4. The fluid F passes the inlet opening 31 parallel to the rotational axis R of the impeller 4 and is distributed through the impeller 4 (indicated by arrows F parallel to the radial direction RD) within the rotational plane 41 towards the first conveying channel 21. At 0° turn angle the volute tongue 23 is arranged in order to separate the fluid entry point 21a from the fluid exit point 21c connected to the outlet opening 32. The first cross section area 21F of the first conveying channel 21 may have any suitable shape providing a conveying channel with similar dimensions parallel and perpendicular to the rotational axis R of the impeller 4. The first cross section area 21F may be a rectangular, oval or circular area depending on the particular application and fluid. In this embodiment the first cross section area has a rectangular shape, in other embodiments the shape might be different, e.g. with rounded edges. In another embodiment the ratio between the sizes of the first cross section areas 21 at the turn angles of 360° (left hand side) and 180° (right hand side) might be less than 1.33.

Figure 4:
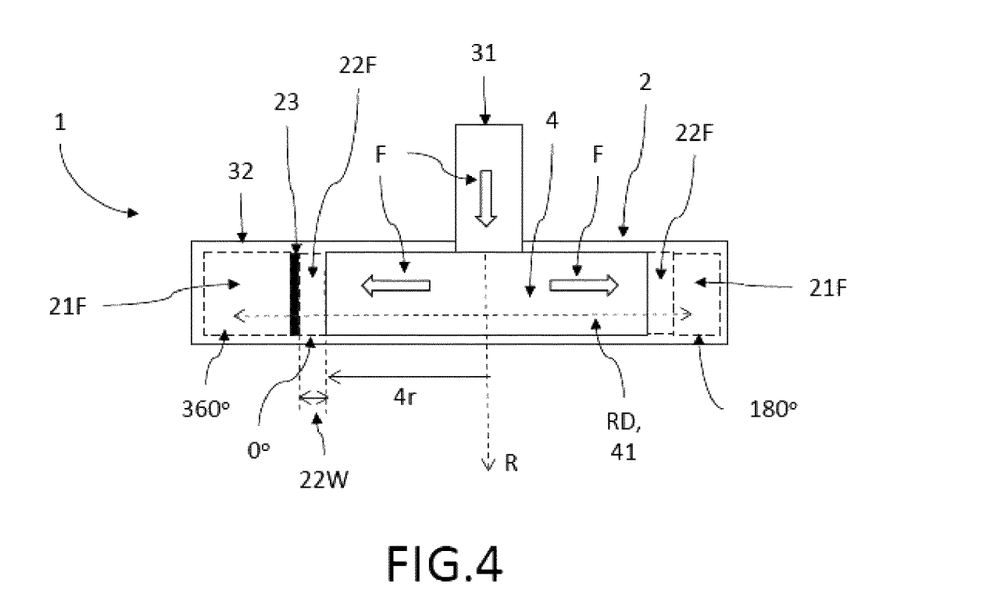
FIG. 4: a schematic view of the first and second cross section areas of the first and second conveying channels at 180° turn angle and at 360° turn angle in a side view of the fluid pump of FIG. 2.

FIG. 4 shows an schematic view of the first and second cross section areas 21F, 22F of the first and second conveying channels 21, 22 at 180° turn angle (right hand side) and at 360° turn angle (left hand side) in a side view of the fluid pump 1 of FIG. 2. The second conveying channel 22 has a width 22W in radial direction RD of the impeller 4 of at least 5%, preferably at least 7%, more preferably at least 10%, of the radius 4r of the impeller 4 at least at the fluid entry point 21a at 0° turn angle. As an example in case of blood pumps as the fluid pump the size of the second cross section area 22F at the entry point 21a at 0° turn angle might be at least 10 mm². In another example the size of the second cross section area at 22F the entry point 21a is additionally below 20 mm². In this embodiment the second conveying channel 22 has a constant size and width 22W for the full turn of the single turn volute.

Figure 5:
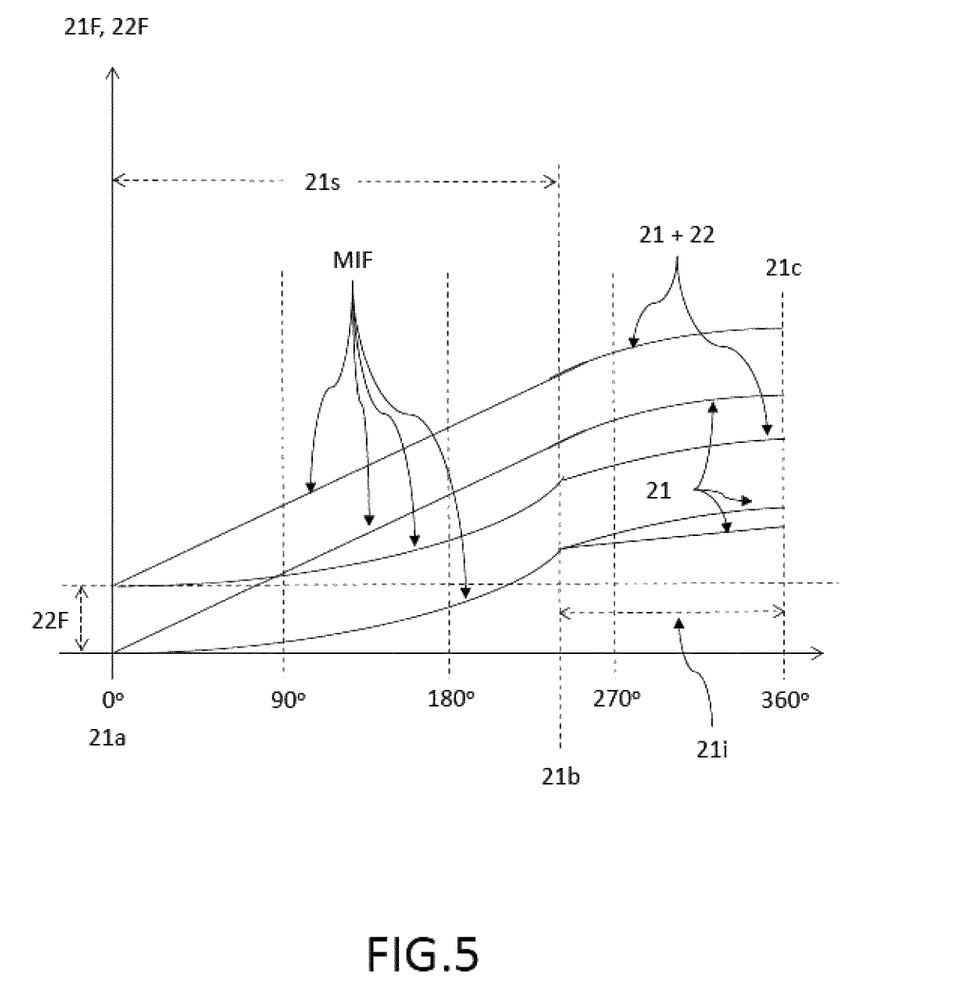
FIG. 5: different embodiments of the monotonic increasing function according to the present invention.

FIG. 5 shows different embodiments of the monotonic increasing function MIF according to the present invention ranging from 0° turn angle to 360° turn angle, which is divided into two parts, the second turn angel interval 21s between 0° turn angle corresponding to the entry point 21a and the first turn angle 21b and followed by the first turn angle interval 21i ranging from the first turn angle 21b to the 360° turn angle corresponding with the exit point 21c for the conveyed fluid out of the single turn volute. For all embodiments the size of the first cross section area 21F continuously increases from 0° turn angle to 360° turn angle. The increase of the size of the first cross section area 21F is described as a function of size depending on the turn angle ranging from 0° turn angle to 360° turn angle denotes here as monotonic increasing function MIF. The term "monotonic" denotes the fact that the size 21F as a function of the turn angle will be constant or increases with the turn angle. A monotonic increasing function of the size 21F over the turn angle does not comprise any intervals, where the size decreases when following the first conveying channel 21 from the fluid entry point 21a at 0° turn angle to the fluid exit point 21c at 360° turn angle. The monotonic increasing function MIF may be a straight line or has a concave shape between the first turn angle 21b and 360° turn angle. In this embodiment the first turn angle 21b is located between 180° and 270° turn angle to provide a turn angle interval 21i of more than 90°. The term straight line denotes a line with a constant slope where a concave shape denotes a function, which second derivate is negative. A concave shape is the opposite shape to a convex shape. In other embodiments the first turn angle 21b may be located at 180° turn angle or less. Here the first turn angle 21b of the monotonic increasing function MIF represents an inflection point of the monotonic increasing function MIF, wherein the monotonic increasing function MIF may increases linearly between the 0° turn angle and the first turn angle 21b or may have a convex shape between the 0° turn angle and the first turn angle 21b. In case of a present second conveying channel 22, the monotonic increasing function MIF at 0° turn angle deviates from zero size by the size of the second conveying channel 22F at 0° turn angle (corresponds to the entry point 21a). In this embodiment the size of the second conveying channel 22F is constant for all turn angles as indicated by the horizontal dashed line providing a constant positive offset 22F of the monotonic increasing function MIF.

Figure 6:
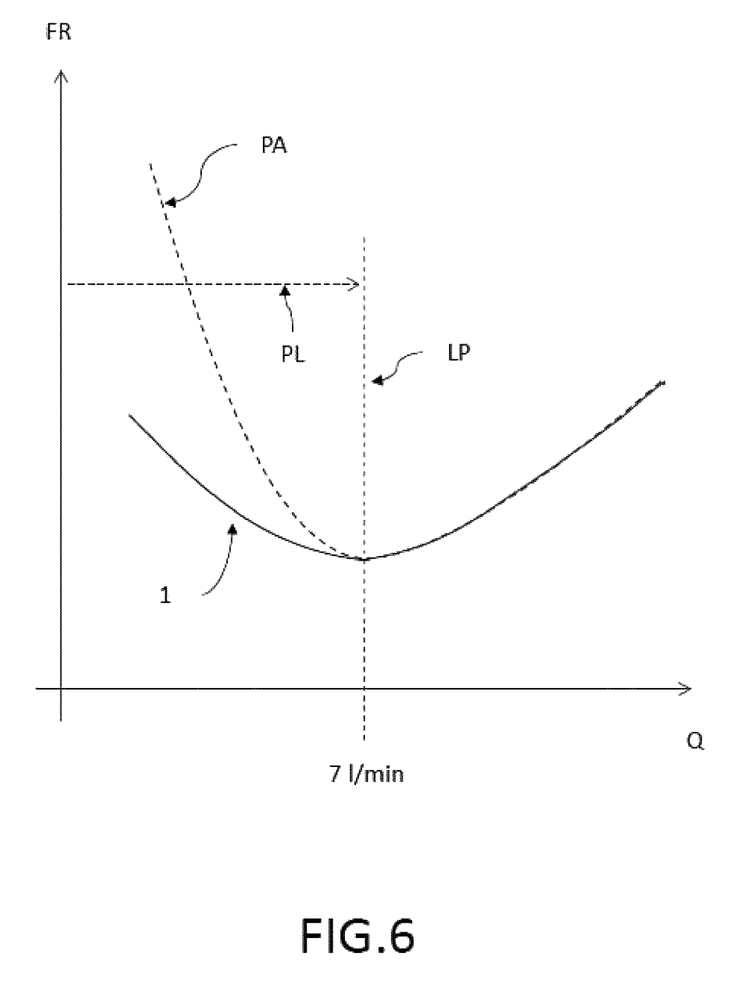
FIG. 6: shows the radially directed forces acting on the impeller as a function of the flow rate of the conveyed fluid for a fluid pump according to the present invention in comparison to a fluid pump according to prior art.

FIG. 6 shows the radially directed forces FR acting on the impeller 4 as a function of the flow rate Q of the conveyed fluid F for a fluid pump 1 according to the present invention in comparison to a corresponding curve PA for a fluid pump according to prior art, where the fluid pumps 1, PA are applied as a blood pumps with blood F as the fluid F. Both blood pumps 1, PA have layout points LP at 7 l/min, where the radially directed hydrodynamic forces FR acting on the impeller 4 have their minima. For flowrates Q higher than the layout point LP and for flow rates Q lower then the layout point LP, the radially directed hydrodynamic forces FR acting on the impeller 4 increase. Average volume flow-rates Q of blood for human beings are approximately at 5 l/min, where the value may be slightly different for males and females. The layout point LP shifted to higher flow rates Q corresponds to so-called oversized blood pumps providing an improved efficiency due to the reduction of the flow resistance caused by the viscosity of blood due to the increased inner dimensions of the conveying housing. As an example blood pumps with a layout point of 5 l/min may have a cross section area at the exit point of approximately 30 mm$^2$, where such oversized blood pumps may have a cross section area at the exit point of approximately 60 mm$^2$. As a result of the oversizing, such oversized blood pumps 1, PA are mainly operated at flow rates Q below the layout point LP (at least more than 50% of the operational time), since the average volume flow rates of blood for human beings of 5 l/min is below the layout point LP. Especially when adapting the housing 2 to provide a layout point LP of 7 l/min, the blood pump 1 is operated nearly all the time (at least more than 90% of the operational time) at or below the layout point LP within the range of partial load PL. For a blood pump PA according to the state of the art, the radially directed forces FR will steeply increase especially for flow rates Q of the operational range of partial load PL, which would be disadvantageous for the bearing layout to bear the impeller, for the required bearing control and for non-disturbed long-time use. The slope of the increases of the radially directed forces FR acting on the impeller 4 depends on the shape of the housing 2 of the blood pump 1. Applying the design rules as specified for blood pumps 1 according to the present invention, the forces FR can be reduced significantly compared to common blood pumps PA in the flow rate Q for partial load PL. Therefore an oversized blood pump 1 according to the present invention provides an efficient fluid pump, where at least the hydrodynamic radially directed forces FR acting of the impeller 4 during operation at partial load PL are significantly smaller compared to fluid pumps PA according to the state of the art.

Figure 7:
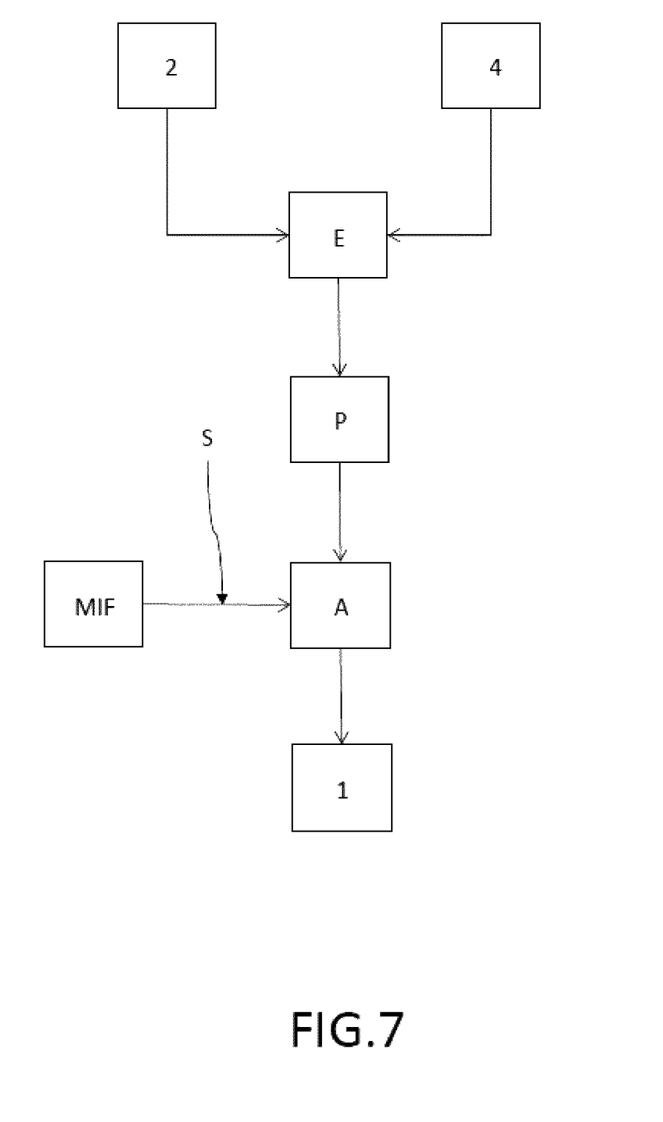
FIG. 7: an embodiment of the method to manufacture the fluid pump according to the present invention.

FIG. 7 shows an embodiment of the method to manufacture the fluid pump according to the present invention as shown in FIG. 1 comprising the steps of establishing E a single turn volute of 360° turn angle within the housing 2 enclosing the impeller 4, providing P a first conveying channel 21 located peripherally around the impeller 4 from a fluid entry point 21a at 0° turn angle to a fluid exit point 21b at 360° turn angle of the single turn volute being connected to the outlet opening 32, where the first conveying channel 21 has a first cross section area 21F in radial direction RD perpendicular to the rotational plane 41 of the impeller 4 and adapting A the first cross section area 21F to have a size increasing as a monotonic function MIF of the turn angle between entry point 21a and exit point 21c, where the monotonic increasing function MIF has a concave shape in a first turn angle interval 21i from a first turn angle 21b to the 360° turn angle at the exit point 21c to increase a velocity of the conveyed fluid F at least in an area 211 assigned to the first turn angle interval 21i. In an embodiment the method comprises the further step of providing a second conveying channel 22 in the single turn volute arranged around the impeller 4 and arranged between the first conveying channel 21 and the impeller 4, where the second conveying channel 22 has a second cross section area 22F in radial direction RD perpendicular to the rotation plane 41 of the impeller 4, where a size of the second cross section area 21F at the fluid entry point 21a of the single turn volute is larger than a predetermined minimum size. Here the friction forces caused by the viscosity of the conveyed fluid F are decreased in order to improve the pumping efficiency. Preferably the second cross section area 22F of the second conveying channel 22 is adapted to reduce the friction forces below a second threshold.

Figure 8:
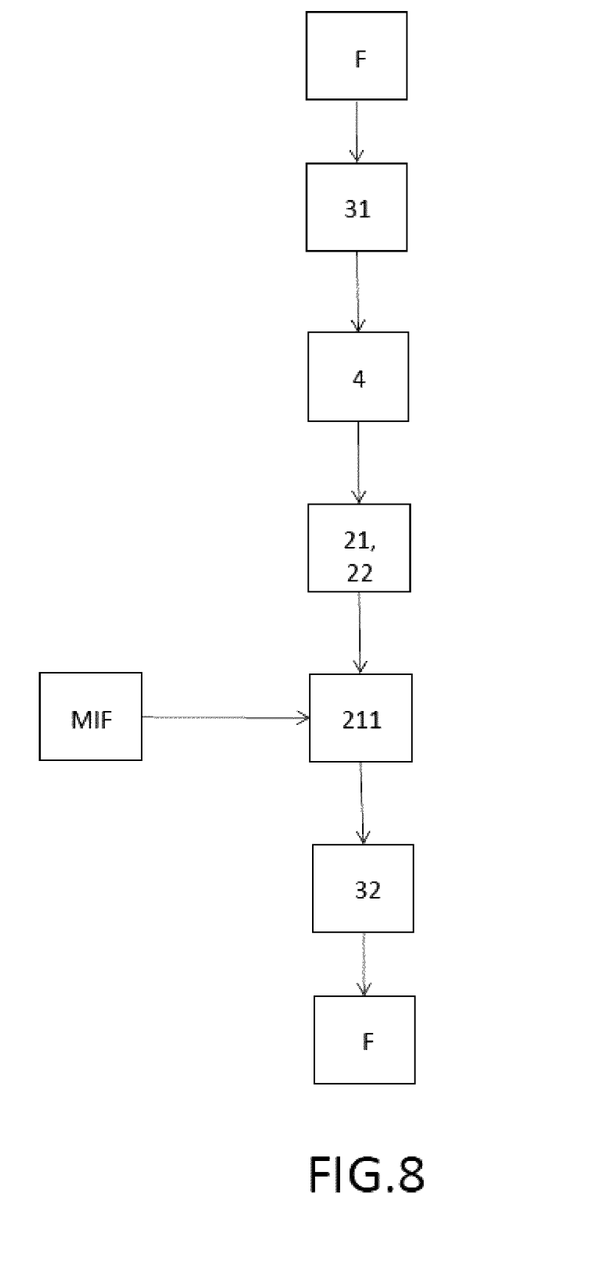
FIG. 8: an embodiment of the method to operate the fluid pump according to the present invention.

FIG. 8 shows an embodiment of the method to operate the fluid pump 1 according to the present invention. As shown in FIGS. 3 and 4, the fluid F enters the inlet opening 31 of the fluid pump 1, passes through the impeller 4 and enters at least the first conveying channel 21 and also the second conveying channel 22, if present. The fluid F is conveyed through the conveying channels 21, 22 into the area 211 of the first conveying channel 21 assigned to the first turn angle interval 21i. Here the shape of the size of the first conveying channel 21 in accordance to the present invention leads to an increase S of the velocity of the conveyed fluid F from a first turn angle 21b to the 360° turn angle at the exit point 21c by a concave shape of the monotonic increasing function MIF within the first turn angle interval 21i.

The method enables to operate the fluid pump with an impeller, where at least the hydrodynamic forces acting of the impeller are smaller compared to fluid pumps according to the state of the art enabling to operate the fluid pump with lower the power consumption required for the bearings and/or enabling to simplify the bearing assembly of the fluid pump, e.g. requiring less bearing components. In an embodiment of the method shown in FIG. 8, where the fluid pump 1 is applied as a blood pump 1 with blood F as the fluid F and where the blood pump 1 has a layout point, at which a function of radially directed hydrodynamic forces acting on the impeller over a flow rate of pumped blood has a minimum and where the layout point is suitably adjusted to flow rates above the average volume flow of blood for human beings to be able to operate the blood pump mainly at partial load, the blood pump 1 is mainly operated at partial load.

While the invention has been illustrated and described in detail in the drawings and the foregoing description, such illustration and description are to be considered illustrative or exemplary and not restrictive.

From reading the present disclosure, other modifications will be apparent to persons skilled in the art. Such modifications may involve other features which are already known in the art and which may be used instead of or in addition to features already described herein.

Variations to the disclosed embodiments can be understood and effected by those skilled in the art, from a study of the drawings, the disclosure and the appended claims. In the claims, the word "comprising" does not exclude other elements or steps, and the indefinite article "a" or "an" does not exclude a plurality of elements or steps. The mere fact that certain measures are recited in mutually different dependent claims does not indicate that a combination of these measures cannot be used to advantage.

Any reference signs in the claims should not be construed as limiting the scope thereof.

LIST OF REFERENCE NUMERALS 1 fluid pump (blood pump)
2 housing
21 first conveying channel
21a fluid entry point (at 0° turn angle)
21b first turn angle
21c fluid exit point (at 360° turn angle)
21i first turn angle interval
21s second turn angle interval
21F first cross section area of the first conveying channel
21I area of the first conveying channel assigned to the first turn angle interval
22 second conveying channel
22F second cross section area of the second conveying channel
22W width of the second cross section area in radial direction
23 volute tongue
31 inlet opening
32 outlet opening
4 impeller
4r radius of the impeller
41 rotational plane of the impeller
A adapting (the size of) the first cross section area
E establishing a single turn volute of 360° turn angle with the housing
F fluid, e.g. blood
FR radially directed hydrodynamic force acting on the impeller
MIF monotonic increasing function
LP layout point
P providing a first conveying channel
PA force curve of a fluid pump according to prior art
PL operation at partial load
Q flow rate of fluid (blood) conveyed through the fluid (blood) pump
R rotational axis of the impeller
RD radial direction (of the impeller)
S increasing the velocity of the fluid

The invention claimed is:

1. A fluid pump for conveying fluids comprising a housing having an inlet opening for receiving the fluid, an outlet opening for discharging the fluid and enclosing an impeller rotating inside the housing to pump the fluid from the inlet opening to the outlet opening and a motor assembly to drive the impeller, wherein the housing is shaped to establish a single turn volute of 360° turn angle providing a first conveying channel located peripherally around the impeller from a fluid entry point at 0° turn angle to a fluid exit point at 360° turn angle of the single turn volute being connected to the outlet opening, where the first conveying channel has a first cross section area in radial direction perpendicular to the rotational plane of the impeller, where a size of the first cross section area increases as a monotonic increasing function of the turn angle between entry point and exit point, where the monotonic increasing function has an average slope and a concave shape in a first turn angle interval from a first turn angle to the 360° turn angle at the exit point, the average slope in the first turn angle interval being smaller than the average slope in a second turn angel interval between 0° turn angle and the first turn angle to increase a velocity of the conveyed fluid at least in an area of the first conveying channel assigned to the first turn angle interval.

2. The fluid pump according to claim 1, wherein the first turn angle is located at a 270° turn angle, preferably at a 180° turn angle, of the single turn volute.

3. The fluid pump according to claim 1, wherein the first turn angle of the monotonic increasing function represents an inflection point of the monotonic increasing function.

4. The fluid pump according to claim 1, wherein the monotonic increasing function increases at least linearly between the 0° turn angle and the first turn angle.

5. The fluid pump according to claim 4, wherein the monotonic increasing function has a convex shape between the 0° turn angle and the first turn angle.

6. The fluid pump according to claim 1, wherein the ratio between the sizes of the first cross section areas at the turn angles of 360° and 180° is less than 1.33.

7. The fluid pump according to claim 1, wherein the housing is further shaped to provide a second conveying channel around the impeller being arranged between the first conveying channel and the impeller, where the second conveying channel has a second cross section area in radial direction perpendicular to the rotation plane of the impeller, where a size of the second cross section area at the fluid entry point of the single turn volute is larger than a predetermined minimum size.

8. The fluid pump according to claim 7, wherein the second conveying channel has a width in radial direction of the impeller of at least 5%, preferably at least 7%, more preferably at least 10%, of the radius of the impeller.

9. The fluid pump according to claim 7, wherein the size of the second cross section area is constant from the fluid entry point at 0° turn angle to the fluid exit point at 360° turn angle of the single turn volute.

10. The fluid pump according to claim 1, wherein the fluid is blood and the fluid pump is applied as a blood pump.

11. The fluid pump according to claim 10, wherein the blood pump has a working point at a certain flow rate, where a function of radially directed hydrodynamic forces acting on the impeller over a flow rate of pumped blood has a minimum and where the working point is adjusted at flow rates above the average volume flow of blood for human beings.

12. A method for manufacturing a fluid pump for conveying fluids as claimed in claim 1 comprising a housing having an central inlet opening for receiving the fluid, an outlet opening for discharging the fluid and enclosing an impeller rotating inside the housing to pump the fluid from the inlet opening to the outlet opening and a motor assembly to drive the impeller, comprising the step of establishing a single turn volute of 360° turn angle within the housing;

providing a first conveying channel located peripherally around the impeller from a fluid entry point at 0° turn angle to a fluid exit point at 360° turn angle of the single turn volute being connected to the outlet opening, where the first conveying channel has a first cross section area in radial direction perpendicular to the rotational plane of the impeller;

adapting the first cross section area to have a size increasing as a monotonic increasing function of the turn angle between entry point and exit point, where the monotonic increasing function has a concave shape in a first turn angle interval from a first turn angle to the 360° turn angle at the exit point to increase a velocity of the conveyed fluid at least in an area assigned to the first turn angle interval.

13. A method for operating a fluid pump for conveying fluids as claimed in claim 1, where the fluid is not blood, comprising a housing having an central inlet opening for receiving the fluid, an outlet opening for discharging the fluid and enclosing an impeller rotating inside the housing to pump the fluid from the inlet opening to the outlet opening and a motor assembly to drive the impeller with at least reduced radial force on the impeller at nominal conditions, wherein the housing is shaped to establish a single turn volute of 360° turn angle providing a first conveying channel located peripherally around the impeller from a fluid entry point at 0° turn angle to a fluid exit point at 360° turn angle of the single turn volute being connected to the outlet opening, where the first conveying channel has a first cross section area in radial direction perpendicular to the rotational plane of the impeller, where a size of the first cross section area increases as a monotonic function of the turn angle between entry point and exit point, comprising the step of increasing a velocity of the conveyed fluid at least in an area assigned to a first turn angle interval from a first turn angle to the 360° turn angle at the exit point by a concave shape of the monotonic increasing function within the first turn angle interval.

* * * * *